United States Patent [19]

Smith

[11] Patent Number: 4,966,755
[45] Date of Patent: Oct. 30, 1990

[54] METHOD AND APPARATUS FOR FUMIGATION OF MATERIALS

[75] Inventor: Colin P. Smith, East Grinstead, England

[73] Assignee: Rentokil Limited, West Sussex, England

[21] Appl. No.: 201,046

[22] Filed: Jun. 1, 1988

[30] Foreign Application Priority Data

Jul. 9, 1987 [GB] United Kingdom ............... 8716133

[51] Int. Cl.⁵ ............. A61L 2/00; A01M 13/00; F04F 1/18
[52] U.S. Cl. ...................... 422/28; 422/30; 422/31; 422/32; 422/37; 422/292; 422/294; 43/125; 239/136; 417/208; 417/439
[58] Field of Search .............. 422/27, 28, 30, 31, 422/32, 34, 35, 37, 292, 294, 305; 417/207–209, 315, 439, 539; 43/125, 129; 239/136, 302, 311, 335, 338; 122/27, 28

[56] References Cited

U.S. PATENT DOCUMENTS

| 810,486 | 1/1906 | Harrison ........................... 122/28 |
| 1,856,931 | 5/1932 | Scott .................................. 422/294 |
| 3,114,599 | 12/1961 | Fanning ........................ 422/30 X |
| 3,255,967 | 6/1966 | Kenney .......................... 43/125 X |
| 3,465,469 | 9/1969 | Winter et al. .................... 43/129 |
| 3,489,505 | 8/1967 | Schumann et al. ........... 422/292 X |
| 3,503,703 | 12/1964 | McDonald et al. ............ 422/292 |
| 4,200,656 | 4/1980 | Cohen et al. ................. 422/37 X |
| 4,282,832 | 8/1981 | Szydlowski et al. ............ 122/28 |
| 4,337,223 | 6/1982 | Kaye .............................. 422/30 X |
| 4,447,399 | 5/1984 | Runnells et al. ............... 422/30 X |
| 4,756,117 | 7/1988 | Friemel ......................... 422/32 X |

FOREIGN PATENT DOCUMENTS

| 068724 | 1/1983 | European Pat. Off. . |
| 475153 | 9/1975 | U.S.S.R. ...................... 422/37 |
| 541171 | 11/1941 | United Kingdom . |
| 914203 | 12/1962 | United Kingdom . |
| 914204 | 12/1962 | United Kingdom . |
| 1206646 | 9/1970 | United Kingdom . |

OTHER PUBLICATIONS

Rentokil Technical Release—Produced by Research & Development Division, No. 101.

Primary Examiner—Robert J. Warden
Assistant Examiner—Rebekah Griffith

[57] ABSTRACT

A method and apparatus for treating a material with gas or vapour, especially a fumigant, comprises a sealable enclosure device, a pump which may have an inlet for the agent and a heat reservoir, and a long flexible hose to allow the enclosure to be evacuated after treatment and the effluent discharged outside the premises where the material is treated.

20 Claims, 3 Drawing Sheets

METHOD AND APPARATUS FOR FUMIGATION OF MATERIALS

This invention relates to treatment of materials, for example goods or structures, with fluids, especially with gases or vapours, and more especially relates to sterilization, dehumidification, and fumigation, and will be described with particular reference thereto. The invention provides methods of treatment and apparatus for carrying out the treatment.

The fumigation of materials to rid them of infestation by a variety of pests, for example, rodents and insects, is a well known procedure. Typically an area is sealed to prevent escape of both the pests and the fumigant (which is often toxic or at best an irritant to humans), the area is subjected to the fumigant for a desired period, and then opened to allow escape of the fumigant.

The need to provide for the subsequent safe dispersal of the fumigant makes the procedure expensive and time-consuming in many cases, especially when the materials to be fumigated are some of the goods in a warehouse. It is the normal procedure to remove the goods concerned to the open air, and cover them with an impermeable sheet, the edges of which are held in contact with the ground by the weight of, for example, a chain placed on the perimeter region of the sheet. After fumigation, the operator, often wearing breathing apparatus, removes the chain and sheet to allow dispersal of the fumigant into the open air. The goods are then returned to the warehouse. The transport of the goods to and fro in an often congested warehouse is time-consuming, and there is increasing concern about the environmental impact of discharging fumigants to the atmosphere. The likelihood of some leakage of fumigant from under the edge of the covering sheet makes it necessary to employ a quantity of fumigant substantially in excess of that theoretically sufficient for the purpose. Furthermore, the probable entry of air, and hence oxygen, prevents the use of fumigants that are non-toxic as such but operate by reducing oxygen concentration, for example, nitrogen or carbon dioxide.

There remains a need, therefore, for a method of treatment, especially fumigation, of materials that may be carried out safely and expeditiously within or close to a building, and apparatus to carry out the treatment.

The present invention provides apparatus for treating a material with an agent in the gaseous or vapour state, which apparatus comprises an enclosure device within which the material may be totally enclosed and sealed, the enclosure device having a port, and means, including a pump or compressor, hereinafter referred to for simplicity as a pump, connectable to the port for transmitting gas or vapour to an outlet in a region remote from the device, the pump being capable, in operation, of pumping gas or vapour to or from the enclosure device through the port.

Advantageously, there is positioned between the port and the outlet, preferably between the port and the pump, a chamber for containing an absorbent. Advantageously, the pump comprises a chamber for containing a heat reservoir, preferably in the form of a particulate material. Advantageously, the pump comprises means for introducing the agent into the chamber.

The enclosure advantageously comprises a base and a cover, which base and cover comprise means, for example at the edge regions of each, for sealably joining the base to the cover.

If, however, the material to be treated may not be moved, for example, where it is machinery that is embedded in a concrete floor, the enclosure may be formed from a cover and the part of the floor beneath and surrounding the material to be treated. In such a case, the cover may be sealed to the floor by means comprising, for example, a strip of mastic laid on the floor in a closed loop surrounding the material, and the edges of the cover pressed down over the mastic to bond it to the floor. Advantageously, this procedure is carried out with the outer surface of the cover contacting the floor and mastic so that an increase in pressure within the enclosure does not tend to peel the cover from the floor and mastic.

Alternatively, there may be permanently or semipermanently mounted in or on the floor around the periphery of such a fixed object means to which the cover may be sealably joined.

The present invention also provides a method of treating a material with an agent in the gaseous or vapour state, which comprises totally enclosing and sealing the material within an enclosure device having a port, connecting the port to means, including a pump, for transmitting gas or vapour to a region remote from the device, treating the material within the device with the agent and, after treatment, pumping any unused agent from the device, and transmitting gas or vapour to an outlet in a region remote from the device. The pump may be at either end of the transmitting means, or between its ends.

The invention further provides fumigation apparatus, which comprises an enclosure device capable of totally enclosing and sealing an article to be fumigated, the device comprising flexible substantially gas- and vapour-impermeable base and cover sheets joined by a substantially gas- and vapour-impermeable sliding clasp fastener, the interior of the device being connected by a port to the outlet of a pump, the pump having an inlet chamber containing a heat reservoir, means for introducing a fumigant into the chamber, and an air inlet to the chamber, whereby a mixture of air and fumigant may be introduced into the device.

The invention still further provides fumigation apparatus, which comprises an enclosure device capable of totally enclosing and sealing an article to be fumigated, the device comprising flexible substantially gas- and vapour-impermeable base and cover sheets joined by a substantially gas- and vapour-impermeable sliding clasp fastener, the device having a first port and a second port, and a pump having an inlet and an outlet, the first port being connected by an inlet line to the inlet of the pump and the second port being connected by an outlet line to the outlet of the pump, whereby air may be circulated by the pump in a path into and out of the enclosure and through the pump, a desiccant being provided in the circulation path.

The invention also provides any novel part or parts of the device or method whether in combination with other described parts or not.

The gas or vapour transmitted may comprise the unused agent together with any products formed as a result of the treatment. Advantageously, however, between the port and the outlet, and preferably between the port and the pump, the treating agent is abstracted from gas or vaporous fluid transmitted to the atmosphere. This may be achieved by absorption of the agent on or in a suitable medium contained, for example, in a chamber in the line connecting port and outlet. The nature of the absorption medium will depend on the nature of the treating agent, as will be discussed more fully below. If the method of treatment includes transmitting the agent to the enclosure device using the pump, and the chamber is located between the port and the pump, it is advantageously readily removable from the line between them, for example by providing a bypass line or by provision of quick connect-disconnect connections.

The source of treating agent may be located within the enclosure device, in which case the pump is necessary only for the removal of agent after treatment. The method of the invention is, however, more especially applicable to a treating agent provided from a source outside the enclosure, advantageously using the pump to transmit the gas or vapour to within the enclosure. In this case, the outlet of the pump is connected to the port but its inlet need not be connected to the line to the remote outlet, although it may be if, for example, air at a temperature different from that obtaining near the pump is required. Suitable treating agents include phosphine, bromomethane and hydrogen cyanide.

By pumping from outside the enclosure the treating agent admixed with air, the preferred method of the present invention avoids, completely or to a large extent, the danger of forming in a fumigation volume strata at lower levels of higher density treating agent at excessive concentration. Such "layering" may result, in prior art methods, either in damage to the material being fumigated at lower levels, ineffective treatment at higher levels, or both these problems. Even when the source of treating agent is within the enclosure device, the use according to the invention of the pump to introduce air at a significant flow rate reduces this danger.

Advantageously, the agent is introduced into the pump from, for example, a pressurized container connected to a feed line that terminates within the pump in a nozzle or other form of small opening or a series of small openings. Advantageously, the agent impinges on a heat reservoir, preferably a bed of particulate material, in a chamber in the pump, thereby mitigating any adverse effects resulting from the cooling associated with any pressure drop or latent heat effects on introducing the agent into the pump. If desired, means may be provided for supplying heat to the heat reservoir. This may be an electrical heater or a gas-powered catalytic heater. The treating agent may advantageously be employed in admixture with air, and there may be provided an air inlet to the pump, and mixing of air and the agent is advantageously effected at this stage.

The enclosure advantageously, as indicated above, comprises a base and a cover, the edge regions of each having means for sealably joining the base and cover together. The base and cover are advantageously completely separable one from another, but it is within the scope of the invention for them to be an integral unit with an opening to allow the material to be treated to be moved into and out of the enclosure.

In a preferred embodiment, the base and cover are both flexible sheets, the base advantageously being a square or a rectangle other than square, and the cover comprising, for example, four sides and a top. A preferred material for the sheet is a plastics material or a metal/plastics laminate, for example aluminium/plastics or aluminized plastics, substantially impermeable to the treating agent being employed. For example, for the fumigant methyl bromide, there may be used polyethylene sheet of thickness about 0.5 mm, optionally reinforced by an open mesh of nylon.

The means for sealably engaging the edge regions of the cover and the base is advantageously a sliding clasp fastener of a type that provides continuous contact between the engaged portions of the cover and base.

Advantageously, the fastener is one comprising cooperating flexible male and female fastener strips, the male strip having a mating rib of generally hook-shaped cross-section, the female strip having a complementary shaped mating groove for interlockingly receiving the rib. The strips are advantageously chamfered at their lower surfaces, to provide a longitudinally extending gap when the strips are interlocked. This gap enables a sliding clasp to exert inward pressure at the lower end of the strips, to cause an opening of the upper ends with consequent disengagement. Examples of such a fastener and of the sliding clasp for convenient opening and closing of it are described in greater detail in British Patent Specifications Nos. 914203 and 914204, the disclosures of which are incorporated by reference herein.

The means for effecting sealing engagement between the parts, especially the edges of the enclosure walls that define an opening through which materials to be treated may be positioned within the enclosure, may be other than as described above. For example, there may be used a strip of double-sided pressure sensitive adhesive tape, in which case the surfaces to be bonded are advantageously arranged so that an increase in pressure within the enclosure tends to strengthen the bond.

Advantageously, there is also provided a means for preventing unauthorized opening of the enclosure. This may comprise, for example, a skirt or valance on the cover, overlapping the engaging means, and which may be secured to the base and locked.

As indicated above, the invention is especially suitable for use when the treatment is one of fumigation, when it is frequently necessary to treat large or unwieldy goods or other materials without moving them out of their immediate area. By the provision of an enclosure device in accordance with an advantageous embodiment of the invention, the device comprising a base sheet and a cover capable of being sealingly joined to each other, the user may readily encapsulate the goods to be fumigated, by laying down the base sheet near the goods, placing the goods on the base sheet, covering the goods with the cover sheet, sealing the cover to the base, and carrying out the remainder of the procedure described herein without the need for time consuming manoeuvres of the goods past other goods in, for example, a warehouse, while still allowing the effluent vapour or gas to be safely discharged outside and away from the treatment area.

An advantage of the procedure according to the invention is that materials treated, especially fumigated or sterilized, for example by ethylene oxide or by methyl formate, by the method may, subsequent to such treatment, be stored in the enclosure device substantially free from the risk of reinfestation. In a preferred procedure, after treatment, and removal of the treating agent from the enclosure device, a supply of fresh air or other suitable atmosphere, advantageously filtered to ensure its freedom from insect and other flying pests and, if desired, of controlled humidity, is pumped into the enclosure device through a port, which is subsequently closed The invention accordingly also provides a method of preserving materials, comprising treating the materials by the method defined above, replacing the treating agent in the enclosure device by a desired atmosphere, and storing the materials in the sealed enclosure device.

It will be understood that a given treatment may have more than one effect. For example, dehumidification, as described in more detail below, may be used to control mites. It also, however, may provide an appropriate atmosphere for long term storage of valuable artifacts.

The enclosure device may be provided with more than one port. This is of advantage if, for example, it is desired to reduce the pressure within or the volume of the enclosure before starting the treatment, or to ensure a flow of gas or vapour to or in a particular part of the enclosure. It is also of advantage if flushing of the enclosure after treatment is desired or required. The port, or any additional port, may be provided with closure means, valves restricting flow to a single desired direction, or reversible valves, as required or desired. Locking means may also be provided for the port or ports.

When extracting a fumigant or other potentially damaging treating agent from the enclosure, the absorption medium mentioned above is advantageously positioned between the port of the enclosure and the pump, its quantity, nature and disposition depending on the treating agent. For fumigants such, for example, as bromomethane or phosphine, activated charcoal has been found suitable. The disposition of any absorbent is advantageously such that flow is maximized consistent with providing adequate contact with the effluent gas or vapour to ensure retention of a significant proportion of the treating agent. The absorption medium is advantageously either fitted into a disposable chamber or arranged in a permanent chamber so that it may readily be removed when the treating agent is being introduced into the enclosure, be replaced by a new supply when exhausted and so that contaminated absorbent may be removed for safe disposal.

The pump is advantageously a centrifugal pump. Where the treating agent, e.g., a fumigant, is introduced by means of the pump, there is advantageously provided, advantageously on the inlet side of the pump, a chamber, which in operation preferably contains a heat reservoir, preferably in the form of a bed of particulate material, and means for introducing the agent into the chamber. Preferably, the means comprises a pipe having an inlet end outside the chamber, the inlet preferably being connectable to an outlet of a container for the treating agent, and an outlet end within the chamber, the outlet preferably comprising an array of apertures positioned to direct the treating agent onto the heat reservoir, if present. As indicated above, air may also be introduced into the pump, conveniently through an inlet to the chamber, where mixing takes place between the agent and the air. A filter is advantageously provided immediately upstream of the pump, at the downstream end of the chamber, and this serves both to prevent dust from the atmosphere reaching the enclosure device and, where the treating agent is supplied from a container of liquid, also to retain any droplets entrained in the gas or vapour and, where used, the air.

The pump, chamber, and agent-introducing means may, for example, for treatment of a volume of approximately 30 m$^3$, be conveniently made by modifying a commercially available industrial vacuum cleaner to provide an apparatus according to the invention.

BRIEF DESCRIPTION OF THE DRAWINGS

One form of apparatus constructed according to the invention, and methods of treatment using it, will now be described in greater detail by way of example only with reference to the accompanying drawings, in which.

Figure 1:
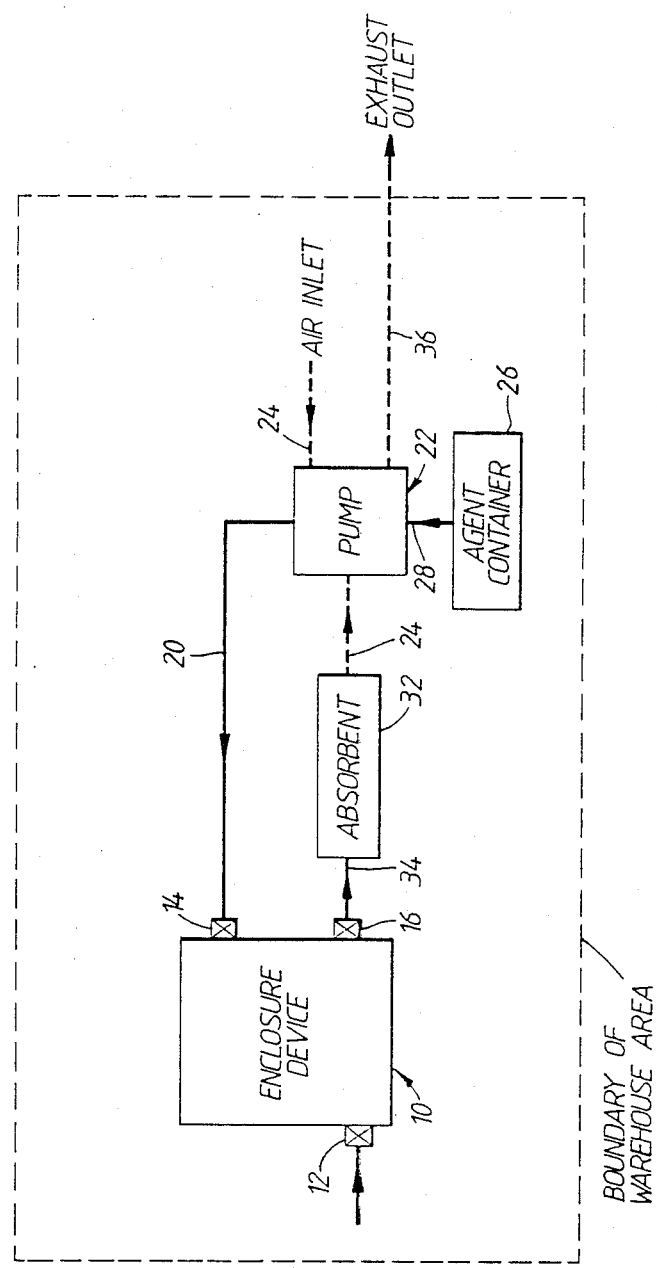
FIG. 1 is a schematic diagram of an apparatus according to the invention.
Figure 4:
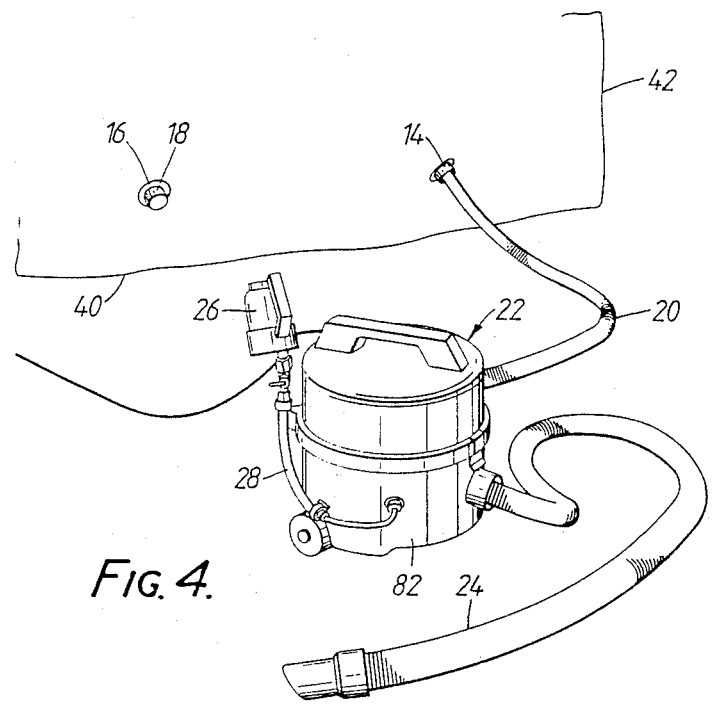
FIG. 4 is a view of the pump and the enclosure device.

Referring now to the drawings, and more especially to FIGS. 1 and 4, there is shown one arrangement of the various components of the apparatus.

An enclosure device, indicated generally by reference numeral 10, is provided with three ports 12, 14 and 16, each of which may be closed by a cap 18. A flexible connector 20 joins the port 14 to a pump indicated generally by the reference numeral 22. A further flexible connector 24 provides an air inlet to the pump. An agent container, in this instance a pressurized container 26 of fumigant, is attached to the pump 22, and an inlet line 28 conveys fumigant to the inlet chamber 30 of the pump 22 as will be described in more detail below. The port 16 may be connected to an absorbent chamber 32 provided with an inlet connection 34. The connector 24 may be used to connect the outlet of the absorbent chamber to the inlet of the pump 22 or may provide direct connection between the port 16 and the inlet of the pump 22. An outlet connection 36 of considerable length may be provided for the pump 22 when exhausting the enclosure device 10 after treatment.

Figure 2:
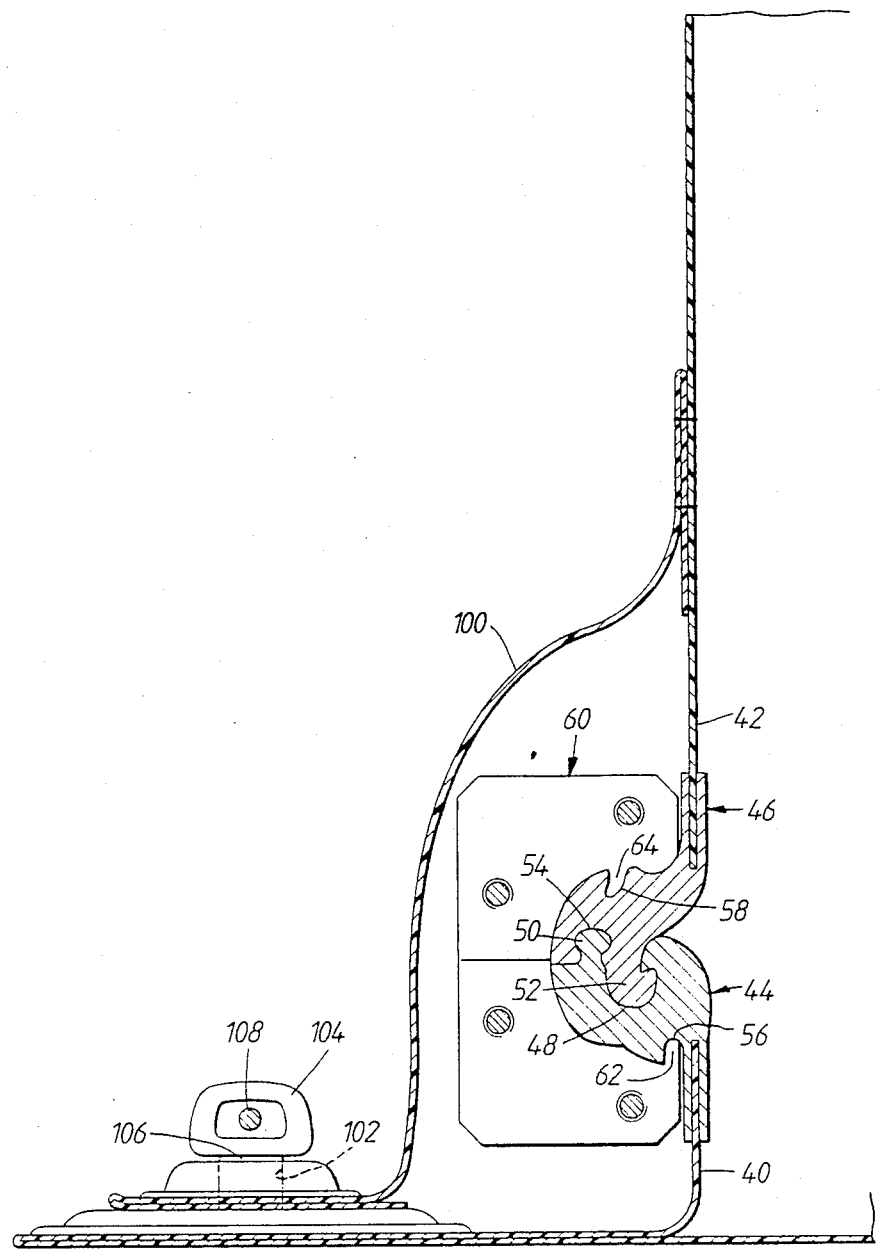
FIG. 2 is a cross-section through a closure member on the enclosure device.

The enclosure device 10 comprises a base sheet 40 and a cover sheet 42. As best seen in FIG. 2, the edge of the base sheet 40 terminates in a female fastener strip indicated generally by the reference numeral 44 and the edge of the cover sheet 42 terminates in a male fastener strip indicated generally by the reference numeral 46. The strip 44 has a groove 48 and an auxiliary rib 50, while the strip 46 has a rib 52, for mating with the groove 48 and an auxiliary groove 54, with which the auxiliary rib 50 mates. The strip 44 has an exterior groove 56, and the strip 46 has an exterior groove 58. A sliding clasp, indicated generally by the reference numeral 60, is shaped at one end with exterior arms terminating in prongs 62 and 64 which engage the grooves 56 and 58 respectively; on sliding the clasp 60 over the strips 44 and 46 with the end shown in FIG. 2 in the trailing direction, the prongs 62 and 64 engage the grooves 56 and 58 to close the strips 44 and 46 into the position shown. The other end of the clasp 60 (not shown) is so shaped as to part the strips 44 and 46 when the clasp is moved in the opposite direction. The reader is referred to British Specifications Nos. 914203 and 914204 for more details of the construction and functioning of the fastener.

The edge region of the cover sheet 42 is provided with a skirt 100 having a series of generally elliptical apertures 102 spaced along its rim. The base sheet 40 is provided with D-rings 104 rotatably mounted on supports 106, the width of the D-rings 104 being such that they may pass through the major axes of the apertures 102 but not through the minor axes. There is provided a cord 108, which is passed through the openings in all the D-rings, tightened, and secured by locking its ends together.

An enclosure device comprising a flexible cover and base sheet as described above has the advantage that goods occupying a volume substantially equal to that of the enclosure may be positioned within it.

Figure 3:
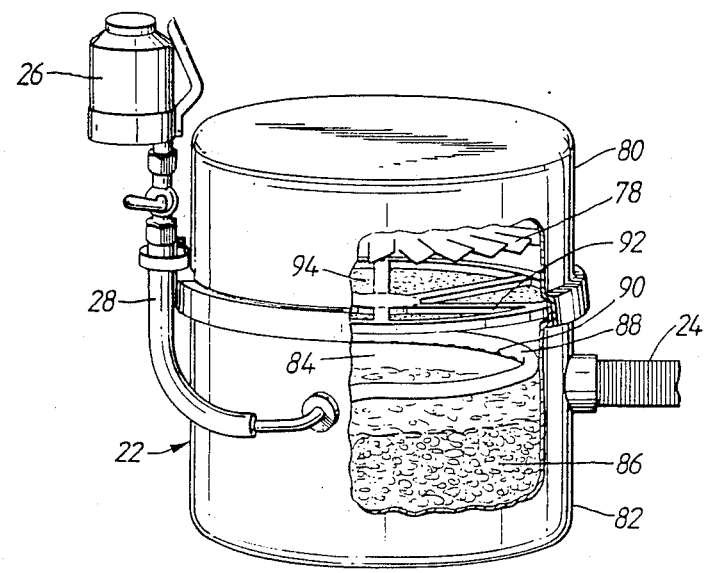
FIG. 3 is a perspective view, partially broken away, of the pump.

Turning now more especially to FIG. 3, the pump 22 comprises an impeller 78 driven by a motor (not shown) in the upper part 80 of a housing, the lower part 82 of which comprises an inlet chamber 84 to the pump. The chamber 84 contains a heat reservoir in the form of copper or granite chips 86, in a bed conveniently of about 7 cm depth. The inlet 28 from the fumigant container 26 enters the chamber through the lower housing 82 and terminates in a C-shaped loop 88 provided with apertures 90. The air inlet 24 also enters the chamber through the lower housing 82. Between the upper and lower parts 80 and 82 there is provided an O-ring seal (not shown) carried on a spider 92 which carries a filter pad 94.

A method of treatment in particular of fumigation in which the fumigant is mixed with air in the pump will first be described. The goods (not shown) are first placed on the base sheet 40, the cover sheet 42 is placed over them and the strips 44 and 46 are put into sealing engagement using the fastener 60. The ports 12 and 14 are closed by caps 18 and the inlet 24 to the pump attached directly to the port 16. The pump 22 is switched on, reducing the volume of air in the enclosure, by this means lowering the air pressure in any tightly packed commodities and reducing fumigation time.

Following this, the port 16 is closed by a cap 18, the inlet 24 of the pump 22 is opened to atmosphere, and the outlet of the pump is connected by the line 20 to the port 14. The pump is switched on, drawing air into the chamber 84 through the inlet line 24 and the container 26 already connected to the line 28 is opened to discharge fumigant through the apertures 90 in the loop 88. The fumigant is directed onto the chips 86 which act as a heat reservoir so that at low temperatures the possibility of a low boiling fumigant, especially one having a high latent heat of boiling, as does bromomethane, merely forming droplets rather than evaporating is minimized. If any droplets are formed, however, they are caught on the filter pad 94 and evaporate there rather than passing into the enclosure device 10 in liquid form. After the dose of fumigant in the container 26 has been exhausted the pump is switched off and the port 14 sealed by a cap 18.

After the necessary fumigation period has elapsed, the inlet line 24 may be connected to the absorbent chamber 32 which is in turn connected via line 34 to the port 16. The outlet of the pump 22 is connected to the outlet line 36 which, if the enclosure device 10 is inside a warehouse, is of sufficient length to extend outside the warehouse. The pump is then switched on and the fumigant is removed from the enclosure device 10, most of it being absorbed in the absorbent chamber 32, or, if an absorbent is not being used, any residues being vented to the atmosphere through the outlet 36. If desired, the ports 12 and 14 may be opened after the volume of the enclosure has been reduced to ensure all fumigant is flushed from the goods by an in-flow of air.

In other methods of treatment, for example, if the fumigant is one which may be positioned in the enclosure device, then the pump need only be used to remove fumigant after treatment. Alternatively, it may also be used to cause an increased flow of air into the device 10 to distribute fumigant vapour more uniformly within the device.

Because of the substantially complete sealability of the enclosure of the present invention, the quantity of treating agent required is substantially less than with prior art methods.

In an alternative mode of operation, the absorbent in chamber 32 may be a desiccant, for example silica gel, and the device operates to dehumidify goods in the enclosure, pumping humid air out through the port 16, drying it by passage through the chamber 32 and returning dry air through the line 20 to the port 14, port 12 being closed. This procedure is used when pests, for example, mites or booklice, are infesting valuable books or artifacts; the reduction in humidity is sufficient to control such infestation with minimal risk of damage to the goods. Accordingly, in this instance the fumigant is air at a relative humidity lower than required by the pests for survival or successful reproduction. In this mode, the location of absorbent or desiccant in the air circulation path is not critical; it could, for example, be placed in the inlet chamber of the pump.

What is claimed is:

1. A method of fumigating a material with an agent in a gaseous or vapour state, which comprises the steps of totally enclosing and sealing the material within a flexible enclosure device having a port, providing means for supplying the agent to the enclosure device, said means including a pump comprising a chamber containing a heat reservoir in the form of a particulate matter, connecting the port to the agent-supplying means, causing the agent to impinge on said particulate matter, fumigating the material within the device with the agent and, after fumigation, pumping any unused agent or gaseous or vaporous reaction products from the device, and transmitting gas or vapour to an outlet in a region remote from the device.

2. A method as claimed in claim 1, wherein the agent is mixed with air in the pump.

3. A method as claimed in claim 1, wherein the particulate matter is granite chips.

4. A method as claimed in claim 1, wherein the fumigant is bromomethane.

5. A method as claimed in claim 1, wherein the gas or vapour pumped from the device after fumigation is passed through an absorbent before being transmitted to the outlet.

6. A method as claimed in claim 1, which also comprises, after the fumigation, pumping air into the device.

7. A method of preserving material which comprises, after carrying out the method of claim 1; pumping a pest-free atmosphere into the enclosure and sealing it.

8. A method as claimed in claim 1, wherein the agent is supplied to an inlet chamber of the pump.

9. A method as claimed in claim 8, wherein the agent is supplied from a source in which it is in liquid form.

10. A method as claimed in claim 1, wherein the enclosure device consists essentially of a base and a cover, each being a flexible sheet.

11. A method as claimed in claim 10, wherein the base and cover are joined by a gas- and vapour-impermeable sliding clasp fastener.

12. Apparatus for fumigating material with a fumigant agent in gas or vapour form, which comprises a flexible enclosure device within which the material may be totally enclosed and sealed, the enclosure device having a port and, connectable to the port, means, including a pump, for transmitting gas or vapour to an outlet remote from the device, the pump comprising a chamber for containing a heat reservoir of particulate matter and being capable, in operation, of causing the agent to impinge on the particulate matter and of pumping gas or vapour to and from the enclosure device through said port.

13. Apparatus as claimed in claim 12, which also comprises a container for absorbent, for positioning between the port and the outlet when the pump is arranged to pump gas or vapour from the device.

14. Apparatus as claimed in claim 12, wherein the pump contains means whereby a fumigant may be introduced into said pump.

15. Apparatus as claimed in claim 12, wherein the enclosure device consists essentially of a flexible base and a cover joined by a gas and vapour impermeable closure means.

16. Apparatus as claimed in claim 15, wherein the closure means is a sliding clasp fastener.

17. Fumigation apparatus which comprises an enclosure device capable of totally enclosing and sealing an article to be fumigated, the device comprising flexible substantially gaş and vapour-impermeable base and cover sheet joined by a substantially gas and vapour-impermeable sliding clasp fastener, the interior of the device being connected by a port to an outlet of a pump, the pump having an inlet chamber for containing a heat reservoir of particulate matter, means for introducing a fumigant into the chamber to impinge on particulate matter therein, and an air inlet to the chamber, whereby a mixture of air and fumigant may be introduced into the device.

18. Fumigation apparatus, which comprises an enclosure device capable of totally enclosing and sealing an article to be fumigated, the device comprising flexible substantially gas- and vapour-impermeable base and cover sheets joined by a substantially gas- and vapour-impermeable sliding clasp fastener, the device having a first port and a second port, and a pump having an inlet and an outlet, the first port being connected by an inlet line to the inlet of the pump and the second port being connected by an outlet line to the outlet of the pump, whereby air may be circulated by the pump in a path into and out of the enclosure and through the pump, a desiccant being provided in the circulation path.

19. A pump having a housing, a first inlet and an outlet, and a second inlet connected to means, outside the pump housing, for supplying a gas or vapour to a chamber in the pump, the chamber also containing a heat reservoir of particulate matter, the second inlet being arranged to direct the gas or vapour toward the heat reservoir.

20. Apparatus for treating material with a fumigating agent in gas or vapour form, which comprises an enclosure device within which the material may be totally enclosed and sealed, the enclosure device having first and second ports and, connectable to the ports, means, including a pump, for transmitting gas or vapour to an outlet remote from the device, the pump comprising a chamber for containing a heat reservoir of particulate matter and being capable, in operation, of causing the agent to impinge on the particulate matter and of pumping gas or vapour to the enclosure device through said first port and from the enclosure device through said second port.

* * * * *